United States Patent [19]

Pierce

[11] 4,296,096

[45] Oct. 20, 1981

[54] HIGH VISCOSITY DENTIFRICE

[75] Inventor: Robert C. Pierce, Plainsboro, N.J.

[73] Assignee: Colgate-Palmolive Company, New York, N.Y.

[21] Appl. No.: 133,706

[22] Filed: Mar. 25, 1980

Related U.S. Application Data

[63] Continuation-in-part of Ser. No. 54,779, Jul. 5, 1979, abandoned.

[51] Int. Cl.$^3$ ............................ A61K 7/16; A61K 7/18
[52] U.S. Cl. .......................................... 424/52; 424/49
[58] Field of Search ................................. 424/49–58, 424/81

[56] References Cited

U.S. PATENT DOCUMENTS

| | | | |
|---|---|---|---|
| 2,798,053 | 7/1957 | Brown | 424/49 |
| 2,923,692 | 2/1960 | Ackerman et al. | 424/81 |
| 2,975,102 | 3/1961 | Matsumura et al. | 424/49 |
| 3,429,963 | 2/1969 | Shedlovsky | 424/56 |
| 3,711,604 | 1/1973 | Colodney et al. | 424/52 |
| 3,956,480 | 5/1976 | Dichter et al. | 424/49 X |
| 4,043,952 | 8/1977 | Ganslaw et al. | 536/1 X |
| 4,090,013 | 5/1978 | Ganslaw et al. | 424/81 X |
| 4,138,477 | 2/1979 | Gaffar | 424/49 X |
| 4,152,420 | 5/1979 | Gaffar et al. | 424/49 X |
| 4,183,914 | 1/1980 | Gaffar et al. | 424/49 X |

OTHER PUBLICATIONS

Chem. Abstracts 89 #130407M, #112149Z (1978), 85 #178639H (1976).

*Primary Examiner*—Shep K. Rose
*Attorney, Agent, or Firm*—Herbert S. Sylvester; Murray M. Grill; Robert L. Stone

[57] ABSTRACT

A dentifrice of high viscosity wherein a water-absorbent anionic polyelectrolyte polymer, such as a polyacrylate, having at least one polyvalent cation, such as aluminum, and having a particle size less than about 74 microns, is employed as gelling agent and also effects the principal humectant function of the dentifrice vehicle.

9 Claims, No Drawings

HIGH VISCOSITY DENTIFRICE

This application is a continuation-in-part of patent application Ser. No. 54,779, filed July 5, 1979, now abandoned.

This invention relates to a dentifrice having rheologically desirable high viscosity.

It is important that a dentifrice such as toothpaste or gel have a high viscosity so that it is not liquid and runny. Of course its viscosity should not be so high that it is difficult to extrude from a toothpaste tube. A viscosity of about 50,000–420,000 cps. e.g. about 60,000–240,000 cps is considered to be a desirable high viscosity for a toothpaste dentifrice (viscosity measured at 10 RPM with #7 spindle on Brookfield Viscometer Model RBF at 22° C.).

Dentifrices have generally been prepared as toothpastes by providing a liquid phase containing water and a humectant, such as glycerine, sorbitol, polyethylene glycol 400 and the like and combining it with a solid phase containing gelling agent such as sodium carboxymethylcellulose, Irish moss, gum tragacanth and the like in proportions to provide a creamy or gel consistency, particularly with a viscosity of about 60,000–240,000 cps. While humectant could be considered optional to the past formulations, its absence would typically result in rapid drying of the product.

It is an advantage of the present invention that a dentifrice is provided of desirable high viscosity (e.g. about 50,000–420,000 cps) wherein the gelling or binding agent is an anionic polyelectrolyte carboxylic acid polymer (that is homopolymer or copolymer) which gelling agent provides humectant character to the dentifrice. Other advantages will be apparent from consideration of the following specification.

In U.S. Pat. No. 3,429,963 to Shedlovsky of Colgate Palmolive Company, dental preparations are described which contain polymeric polyelectrolytes including polyacrylic acid and polyacrylates as anticalculus agents. This patent also indicates that certain of the polyelectrolytes therein disclosed can provide gelling characteristics. However, these polyelectrolytes do not correspond to the defined polyelectrolytes of the present invention which also provide humectant effect. Similar remarks also apply to other disclosures of polyacrylic compounds for dentifrices, such as in U.S. Pat. Nos. 2,798,053 to Brown; 2,975,102 to Matsumura et al; 2,980,655 to Glass et al; 3,574,822 to Shepard et al; 3,904,747 to Cordon et al; 3,914,405 to Shepard et al; 3,934,001 to Watson; and 4,003,971 to Mannara.

In accordance with certain of its aspects this invention relates to a dentifrice comprising as a gelling agent which further provides a humectant characteristic to the dentifrice, water-absorbent anionic polyelectrolyte polymer surface treated with at least one polyvalent metal cation and having a particle size such that at least about 90% of the particles are less than 500 microns and about 99% of the particles are larger than 2 microns.

The anionic polyelectrolyte polymer is the type of material described in U.S. Pat. No. 4,043,952 to Ganslaw et al. This Ganslaw et al. patent at column 2, lines 5 et seq. incorporates by reference U.S. Ser. No. 556,291, filed Mar. 7, 1975 which is now U.S. Pat. No. 4,090,013, granted May 16, 1978, to Ganslaw et al. Both Ganslaw et al. patents are incorporated herein. As stated therein there are three classes of water-absorbent materials; the water-soluble compositions, the covalently cross-linked water-insoluble compositions, and the ionically complexed water-insoluble compositions.

The absorbent compositions of matter of the first class (water-soluble) are poly-electrolytes comprising natural or synthetic polymers characterized by substantial water-solubility in an aqueous medium and by the presence of anionic groups (preferably carboxyl, sulfonate, sulfate or phosphate anionic groups). The preferred natural polymers are the anionic derivatives of starch or cellulose, and the preferred synthetic polymers are the carboxylic acid homopolymers or copolymers containing at least 20 mole percent carboxylic acid units e.g., polyacrylic acid.

Exemplary of the carboxylic acid-containing polyelectrolytes are the synthetic copolymers of ethylenically unsaturated monomers with mono-ethylenically unsaturated carboxylic acid or their partially neutralized salts. Examples of the preferred $\alpha,\beta$-mono-unsaturated carbyxylic acids include acrylic acid, methacrylic acid, maleic acid, maleic anhydride, itaconic acids, itaconic anhydride, fumaric acid, half esters or half amides of maleic, fumaric and itaconic acid, crotonic acid, etc. Examples of the preferred $\alpha,\beta$ethylenically unsaturated monomers include acrylamide or methacrylamide and their N and N,N dialkyl derivatives containing 1–18 carbon alkyl groups, alkyl acrylates and methacrylates containing 1–18 carbon alkyl groups, vinyl esters, vinyl aromatic compounds, dienes, etc.

Homopolymers of monoethylenically unsaturated carboxylic acids or mixtures of these monomers may also be used. Examples include acrylic and methacrylic acid homopolymers and acrylic acid/methacrylic acid copolymers.

Exemplary of the sulfonic acid-containing poly-electrolytes are the homopolymers of monoethylenically unsaturated sulfonic acids (or salts thereof) and copolymers thereof with the aforementioned ethylenically unsaturated monomers. Suitable sulfonate-containing monomers include aromatic sulfonic acids (such as styrene sulfonic acids, 2-vinyl-3-bromobenzenesulfonic acid, 2-vinyl-4-ethylbenzensulfonic acid, 2-alkyl benzene sulfonic acid, vinylphenylmethane-sulfonic acid and 1-sulfo-3-vinylphenylmethane sulfonic acid), heterocyclic sulfonic acids (such as 2-sulfo-4-vinylfurane and 2-sulfo-5-allylfurane), aliphatic sulfonic acids (such as ethylenesulfonic acid and 1-phenylethylene sulfonic acid), sulfonic acids containing more than a single acid radical (such as $\alpha$-sulfoacrylic acid and $\alpha$-sulfoethylenesulfonic acid), and sulfonic acid derivatives hydrolizable to the acid form (such as alkenyl sulfonic acid compounds and sulfoalkylacrylate compounds).

Exemplary of the sulfate-containing poly-electrolytes are those formed by reacting homopolymers and copolymers containing hydroxyl groups or residual polymer unsaturation with sulfur trioxide or sulfuric acid; for example, sulfated polyvinyl alcohol, sulfated hydroxyethyl acrylate, sulfated hydroxypropyl methacrylate. Exemplary of the phosphate-containing poly-electrolytes are the homopolymers and copolymers of ethylenically unsaturated monomers containing a phosphonic acid moiety, such as methacryloxy ethyl phosphate.

Exemplary of the poly-electrolytes formed of natural polymers and their derivatives are the carboxylated, sulfonated sulfated, and phosphated derivatives of cellulose and starch, such as carboxymethyl cellulose and carboxymethyl starch. Naturally occurring anionic poly-electrolytes such as alginates, carrageenen, proteins (such as gelatin, casein, and soya protein), gum arabic, algin, gum chati also have utility.

The poly-electrolytes polymers may be prepared by conventional polymerization techniques, such as solution, emulsion, suspension, and precipitation polymerization techniques. While the polymers are preferably prepared using a free radical polymerization mechanism, other polymerization mechanisms, including anionic and cationic mechanisms, may be used. The polyelectrolyte generally has a molecular weight of from 10,000 to 10,000,000.

The absorbent composition of matter of the second class (water-insoluble covalently -crosslinked) may be formed from anionic poly-electrolytes of the first class which have been covalently crosslinked to render them water insoluble, yet water-swellable. Typically polyfunctional compounds, such as divinyl benzene, are copolymerized with the poly-electrolyte monomer of prepolymer so as to enter into a plurality of poly-electrolyte polymer chains or attach to the available dependent functional groups of a plurality of polymer chains. Conventional polymerization techniques including ultraviolet and other radiation initiated polymerization mechanisms, may be used. Examples of suitable polyfunctional compounds include divinyl compounds (such as divinyl benzene, divinyl diethylene glycol diether, divinyl diphenyl silane and divinyl sulfone), allyl compounds (such as triallyl cyanurate, trimethylol propane diallyl ether, allyl methacrylate, allyl acrylate, allyl crotonate, diallyl phthalate, diallyl succinate and diallyl sucrose), polyfunctional acrylates and methacrylates (such as tetraethylene glycol diacrylate, triethylene glycol dimethacrylate, pentacrythritol tetra-acrylate, ethylidene dimethacrylate, and trimethylol propane trimethacrylate), and polyfunctional acrylamides and methacrylamides (such as N,N'-methylene bis-acrylamide, and N,N'-methylene bis-methacrylamide, etc).

An absorbent composition of this second class (like one of the third class described hereinbelow) is defined as providing a gelatinous agglomerate of liquid-swollen particulate members in the presence of a quantity of body exudate, as capable of absorbing at least about fifteen times its weight in body exudate, and as capable of retaining the absorbed exudate when exposed to pressure sufficient to deform the agglomerate.

The absorbent compositions of the third class (water-insoluble ionically complexed) may be formed from anionic polyelectrolytes of the first class which have been ionically complexed to render them water-insoluble, yet water-swellable. A polyvalent metal cation is used to complex the poly-electrolyte to render the overall polymer composite substantially insoluble yet highly swellable in aqueous media. The cations have a valence of at least three and are cations of metals belonging to the following groups of the Periodic Table: IIIB, IVB, VB, VIB, VIIB, VIII, IIIA, IVA, VA, VIA. The preferred metals are orally acceptable, such as aluminum, zirconium and iron. Aluminum is an especially preferred metal.

The metal compound used to contribute the cation can be added prior to polymerization of the monomers of the polyelectrolyte, during polymerization or postadded to a polymeric polyelectrolyte solution, the only restraint being that the poly-electrolyte compound be at least ionizable or soluble in the system. The polyvalent metal can be added to the composition by means of a basic, acidic or neutral salt, hydroxide, oxide or other compound or complex which has at least limited solubility in water or an organic solvent in which the polyelectrolyte and its constituent monomers are also soluble at the time of cation introduction.

Examples of inorganic salts include chlorides, nitrates, sulfates, borates, bromides, iodides, fluorides, nitrides, perchlorates, phosphates, and sulfides, such as aluminum chloride, aluminum sulfate, ferric sulfate, ferric nitrate and zirconium chloride. Examples of organic salts include salts of carboxylic acids such as carbonates, formates, acetates, butyrates, hexanoates, adipates, citrates, lactates, oxalates, oleates, propionates, salicylates, glycinates, glycollates and tartrates; for example, aluminum formoacetate, basic aluminum acetate, aluminum citrate aluminum diformate, aluminum triformate, ferric acetate, aluminum octate, ferric oleate, zirconium lactate and zirconium acetate.

The ammonia and amine complexes (and especially those coordinated with ammonia) of these metals are particularly helpful. Amines capable of so complexing include morpholine, monoethanol amine, diethylaminothanol and ethylenediamine. Examples of these amine complexes include ammonium zirconyl carbonate, ammonium zirconyl glycinate, and ammonium zirconium chelate of nitrilotriacetic acid. Polyvalent metal complexes (salts) of organic acids that are capable of solubilization in an alkaline pH range may also be employed. Such anions as acetate, glutamate, formate, carbonate, salicylate, glycollate, octoate, benzoate, gloconate, oxalate and lactate are satisfactory. Polyvalent metal cholates wherein the ligand is a bidentate amino acid, such as glycine or alanine, are particularly useful.

Other organic compounds containing polyvalent metals are also useful; for example, the metal alkoxides, metal alkyls, and acetyl acetonates, such as aluminum isopropoxide, aluminum acetyl acetonate, zirconium ethoxide and triethyl aluminum.

The cations of one or more of such metals are present in the absorbent composition at a level of 0.01–5.0 milliequivalents of cation per gram of poly-electrolyte, and preferably 0.1–1.0 milliequivalents of cation per gram of polyelectrolyte. Lower cation levels do not render the polymeric composition water-insoluble, while higher cation levels render the polymer composition not only water-insoluble, but also non-swellable.

Lower cation levels within the range are especially effective when the poly-electrolyte is of relatively high molecular weight. Regardless of pH, higher cation levels within the specified range contribute to the permanence of the gel formed by exposure of the dried complex the fluid to be absorbed. In general it has been found that the optimum cation level varies with the ion size of the cation.

As will be recognized by those familiar with the art of complexing, not all of the available ionic linkages of a given polyvalent cation will necessarily be associated with different poly-electrolyte polymeric chains, especially in the case of the cations, such as zirconium, having valence or oxidation states greater than 3, inner salts formation (that is, the attachment of a single cation exclusively to a single polymeric chain or to a number of polymer chains less than the valence) will occur to an unspecified degree dependent on the spatial geometries presented by the reagents involved, relative concentrations, etc.

The absorbency of the composition is improved when the poly-electrolyte is at higher molecular weight levels within the specified range of 10,000 to 10,000,000. Accordingly, various di-functional monomers such as allyl methacrylate may be used to chain extend the poly-electrolyte prior to exposure to the cation. The amount of chain extender used must, of course, not render the poly-electrolyte insoluble in aqueous media. The increased chain length of the poly-electrolyte permits lower cation levels to be employed as there are fewer polymer chains to be complexed.

The absorbency of the composition is also improved when the poly-electrolyte has up to about 95%, preferably 40–85%, of its anionic groups neutralized with a suitable base such as an alkali metal hydroxide, as primary, secondary or tertiary amine, etc. The neutralization acts to uncoil and straighten out the polymer chains in aqueous fluids so that the final complex is more swellable in the presence of such fluids.

The poly-electrolytes must be substantially water-soluble at some pH between 2.0 and 8.5 to utilize the metal complexing and form the desired water-insoluble absorbent complex. However, the reversibility of ionic complexing (as opposed to covalent bonding) is well known in the chemical art and once the pH of the complex is raised above a certain level (i.e. the pH of reversibility), the complex breaks down, yielding again the water-soluble non-absorbent poly-electrolyte. The acid strength of the poly-electrolyte acid has a marked effect upon the pH of reversibility. The higher the acid strength (i.e. the lower the pH of dissociation), the lower the pH of reversibility. For example, polyacrylic acid, a weak polymeric acid, reverses its complex at pH 8.5–9.0 whereas styrene sulfonic acid, a very strong polymeric acid, reverses its complex at a pH of about 3.5–5.0.

The preferred composition is a polyacrylic acid aluminum cation complex. The aluminum cation is typically added (as aluminum acetate) during precipitation polymerization of the acrylic acid with a free radical catalyst, to provide about 0.3 milliequivalents of aluminum per gram of polymer, according to the following formulation:

| PARTS BY WEIGHT | INGREDIENTS |
| --- | --- |
| 73.07 | potassium acrylate |
| 27.74 | acrylic acid |
| 0.19 | allyl methacrylate |
| 1.49 | basic aluminum acetate |

In both the second and third classes of absorbent compositions (the water-insoluble ones), the formation of a light-to-moderate network of linkages between polymer chains—in one case covalent linkages and in the other case ionic linkages—renders the composition water-insoluble, but water-swellable. The dry absorbent composition is rendered, in the presence of a quantity of body exudate or other water-containing material into a gelatinous agglomerate of liquid-swollen particulate members. The composition is capable of absorbing at least 15 times its weight in body exudate, and generally at least 40 times its weight. Furthermore, the composition is capable of retaining the absorbed exudate even when exposed to pressure sufficient to deform the agglomerate, and generally up to pressures of about 2.5 psi.

The polyvalent metal cations useful in the present invention preferably have a valence of at least three and are preferably aluminum, zirconium and iron. Aluminum is an especially preferred metal.

The polyvalent metal compound providing the polyvalent metal cation can be added to the dispersing medium before, with or after the absorbent composition of matter. The only restraint on selection of the polyvalent metal compound is that it must be at least ionizable or soluble in the dispersing medium. Thus the polyvalent metal cations can be added to the dispersing medium by means of a basic, acidic or neutral salt, hydroxide, oxide, or other compound or complex which has at least limited solubility in the dispersing medium.

Examples of suitable inorganic salts include chlorides, nitrates, sulfates, borates, bromides, iodides, fluorides, nitrides, perchlorates, phosphates, and sulfides, such as aluminum chloride, aluminum sulfate, ferric sulfate, ferric nitrate, and zirconium chloride. Examples of suitable organic salts include salts of carboxylic acids such as carbonates, formates, acetates, butyrates, hexanoates, adipates, citrates, lactates, oxalates, oleates, propionates, salicylates, glycinates, glycollates and tartrates; for example, zinc acetate, aluminum formoacetate, basic aluminum acetate, aluminum citrate, aluminum diformate, aluminum triformate, ferric acetate, aluminum octate, zirconium lactate and zirconium acetate. Basic aluminum acetate is a preferred organic salt.

The ammonia and amine complexes (and especially those coordinated with ammonia) of these metals are particularly useful. Amines capable of so complexing include morpholine, monoethanol amine, diethylaminoethanol and ethylediamine. Examples of these amine complexes include ammonium zirconyl carbonate, ammonium zirconyl glycinate, and ammonium zirconium chelate of nitrilotriacetic acid. Polyvalent metal complexes (salts) or organic acids that are capable of solubilization in the dispersing medium may also be employed. Such anions as acetate, glutamate, formate, carbonate, salicylate, glycollate, octoate, benzoate, gluconate, oxalate and lactate are satisfactory. Polyvalent metals chelates wherein the ligand is a bidentate amino acid, such as glycine or alanine, are particularly useful.

Other organic compounds containing polyvalent metals are also useful; for example, the metal alkoxides, metal alkyls, and acetyl acetonates, such as aluminum isopropoxide, aluminum acetyl acetonate, zirconium ethoxide and triethyl aluminum.

The cations of one or more of such metals are provided at a level of 0.05–10.0 milliequivalents of cation per gram of the absorbent composition of matter on a dry basis, and preferably 0.1–2.0 milliequivalents of cation per gram. In general, the finer the particle form of the dry absorbent composition, the more cation should be employed.

The most preferred anionic polyelectrolytes are polyacrylates surface treated or cross linked with aluminum particularly as available from National Starch and Chemical Corporation of Bridgewater, N.J., U.S.A. under the trademark Permasorb. Those polyacrylates are smaller than 590 microns (300 mesh) and about 99% of the particles are larger than 2 microns are effective as gelling agents which provide substantial humectant character to a dentifrice. Preferably the particles are substantially between about 74 microns and about 15 microns, to provide optimum creamy character without difficulty to wet the dentifrice.

A preferred particle size distribution for a polyacrylate in accordance with this invention is

TABLE 1

| MICRONS | U.S. STANDARD SIEVE MESH | WEIGHT PERCENT RETENTION ON SIEVE |
|---|---|---|
| 149 | ON 100 | 0.0716 |
| 74 | ON 200 | 0.329 |
| 44 | ON 325 | 1.25 |
|  | THRU 325 | 98.35 |

The mean size is about 30 microns.

The gelling agent can comprise about 0.5-20% by weight of the dentifrice, preferably about 0.5-3%. Generally, the water-absorbent polyelectrolyte polymer is the sole gelling agent. However, if desired, rheological modifications in the character of the dentifrice can be effected by including a minor proportion (e.g. up to about half the amount of the electrolyte) of an additional gelling agent, such as sodium carboxymethyl cellulose, Irish moss, gum tragacanth and the like.

Typical anionic polyelectrolytes have the following particle size distribution:

TABLE 2

| MICRONS | U.S. STANDARD SIEVE MESH | PERMASORB® 30 | PERMASORB® 10 | PERMASORB® 10 (THRU 200 MESH) | PERMASORB® AEROSOL |
|---|---|---|---|---|---|
| 590 | 30 | 2.6 | 10.1 | 0 |  |
| 420 | 40 | 37.0 | 29.8 | 0 |  |
| 250 | 60 | 51.9 | 46.7 | 0 |  |
| 149 | 100 | 6.3 | 10.6 | 0.0716 |  |
| 74 | 200 | 1.1 | 1.8 | 0.329 |  |
| 44 | 325 | 1.1 | 1.0 | 1.25 |  |
| LESS THAN 44 |  |  |  |  |  |
|  | THRU 325 | — | — | 98.35 |  |
|  |  |  |  | 30 MICRON MEAN SIZE |  |
| 30.0 |  |  |  |  | 1.0 |
| 20.0 |  |  |  |  | 1.0 |
| 15.0 |  |  |  |  | 6.0 |
| 10.0 |  |  |  |  | 34.0 |
| 8.0 |  |  |  |  | 20.0 |
| 6.0 |  |  |  |  | 17.0 |
| 4.0 |  |  |  |  | 13.0 |
| 2.0 |  |  |  |  | 7.0 |
| Less than 2.0 |  |  |  |  | 1.0 |
|  |  |  |  |  | 9.5 MICRONS MEAN SIZE |

Permasorb® 10 (through 200 mesh) is preferred.

The liquid phase of the dentifrice may be water in amount of up to about 89.5% by weight. If it is desired to modify the rheological character of the dentifrice a humectant may be used in addition to the humectant effect provided by the anionic polyelectrolyte. Such humectant may be glycerine, sorbitol, polyethylene glycol 400 and the like and may be present in amount up to about 20% by weight of the dentifrice. While such humectant may be absent, preferably it is present in amount of about 2-10% by weight of the dentifrice. The preferred humectant is glycerine.

A normally water-insoluble dentally acceptable polishing agent is dispersed in the dentifrice vehicle. Polishing agents are particularly important ingredients in dentifrices, performing an important mechanical cleaning function. The polishing agents are usually finely divided water insoluble powdered materials of particle size such that they pass a 140 mesh screen, U.S. Standard Sieve Series. Preferably, they are from 1 to 40 microns, most preferably from 2 to 20 microns in particle size, with distribution of particle sizes being normal over the range.

Among the polishing agents that are useful in the preparation of dentifrices may be mentioned dicalcium phosphate, tricalcium phosphate, insoluble sodium metaphosphate, crystalline silica, colloidal silica, complex aluminosilicates, aluminum hydroxide (including alpha-alumina trihydrate), magnesium phosphate, magnesium carbonate, calcium carbonate, calcium pyrophosphate, bentonite, talc, calcium silicate, calcium aluminate, aluminum oxide, aluminum silicate, and silica xerogels. The above listing of polishing agents, and other listings of other constituents of the dentifrice composition given in the present specification are not intended to be exhaustive. Therefore, for other materials of these types reference should be made to a standard handbook, such as Cosmetics Science and Technology, by Sagarin, 2nd printing, 1963, published by Interscience Publishers, Inc.

The content of polishing agent in the final dentifrice product is variable; for example, in the manufacture of commercially acceptable form-retaining extrudible dental creams there usually will be present 20 to 75% of polishing agent, e.g., dicalcium phosphate. The preferred proportions of such constituents are 40 and 60% respectively.

Any suitable surface active or detersive material may be included in the dentifrice compositions. Such compatible materials are desirable to provide additional detersive, foaming and antibacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulfate, higher alkyl sulfate (e.g., sodium lauryl sulfate), alkyl aryl sulfonate (e.g. sodium dodecyl benzene sulfonate, higher fatty acid esters of 1,2-dihydroxy propane sulfonate) and the like.

The various surface active materials may be used in any suitable amount, generally from about 0.05 to about 10% by weight, and preferably from about 0.5 to 5% by weight of the dentifrice composition.

It is a further embodiment of the present invention to use the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycerine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or perferably as the water-soluble salts thereof, such as the alkali metal, ammonium, amine and alkyolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein, references to "amino carboxylic acid compound," "sarcoside," and the like refers to such compounds having a free carboxylic group or the water-soluble carboxylic salts.

The compositions of the present invention suitably may also contain a fluorine-containing compound having a beneficial effect on the care and hygiene of the oral cavity, e.g., dimunution of enamel solubility in acid and protection of the teeth against decay. Examples thereof include sodium fluoride, stannous fluoride, potassium fluoride, potassium stannous fluoride ($SnF_2KF$), sodium hexafluorostannate, stannous chlorofluoride, sodium fluorizirconate, and sodium monofluorophosphate. These materials which dissociate or release fluorine containing ions in water, suitably may be present in an effective but non-toxic amount, usually within the range of about 0.01–1% by weight of the water soluble fluorine content thereof.

The preferred fluorine-containing compound is sodium monofluorophosphate, typically present in amount of 0.076–7.6% by weight, preferably about 0.76%. When fluorine-containing compound is present, it is preferred that the anionic polyelectrolyte carboxylic acid polymer be present in amount of about 0.5–2% by weight.

Various materials may be incorporated in the oral preparations of this invention. Examples thereof are coloring or whitening agents, preservatives such as sodium benzoate, silicones, chlorophyll compounds and ammoniated materials such as urea, diammonium phosphate and mixtures thereof. These adjuvants are incorporated in the instant compositions in amounts which do not substantially adversely affect the properties and characteristics suitably selected and used in proper amount depending upon the particular type of preparation involved.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl) biguanide;
p-chlorophenyl biguanide;
4-chlorobenzylhydryl biguanide;
4-chlorobenzhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyldimethylammonium) octane dichloride;
5,6 dichloro-2-guanidinobenzimidazole;
$N^1$-p-chlorophenyl-$N^5$-laurylbiguanide;
5-amino-1,3 bis(2-ethylhexyl)-5-methylhexahydropyrimidine; and their non-toxic acid addition salts Any suitable flavor or sweetener may be employed in formulating a flavor for the compositions of the present invention. Suitable flavors are less volatile than chloroform. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Saccharin acid provides sweetening to the dentifrice. Suitable sweeteners include saccharin, sucrose, lactose, maltose, sorbitol, sodium cyclamate, dipeptides of U.S. Pat. No. 3,939,261 and oxathiazon salts of U.S. Pat. No. 3,932,606 may be employed. Suitably, flavor and sweetening agent may together comprise from about 0.01 to 5% weight.

The dental creams should have a pH of about 5.0 to 9.0 preferably about 6.0 to 7.5. The reference to the pH is meant to be the pH determined directly on the dental cream before it is aged.

The dentifrice of the present invention may be prepared by making a pre-mix of water and anionic polyelectrolyte and additional gelling agent, if employed, adding thereto humectant if employed and then mixing with polishing agent, if employed. Thereafter the system is thoroughly mixed in a planetary mixer to allow for complete swelling of the anionic polyelectrolyte while under vacuum. Thereafter, surface active agent and flavor may be added.

Alternatively, the pre-mix contain water and humectant with the anionic polyelectrolyte added thereto.

The following specific example is further illustrative of the nature of the present invention, but it is to be understood that the invention is not limited thereto. The compositions are prepared in the indicated manner and all amounts of the various ingredients are by weight unless otherwise specified.

EXAMPLE

The following dentifrices are prepared in the manner indicated:

| | PARTS | | |
|---|---|---|---|
| | A | B | C |
| Water | 47.1 | 44.9 | 39.9 |
| Sodium benzoate | 0.50 | 0.47 | 0.52 |
| Tetrasodium pyrophosphate | 0.50 | 0.47 | 0.52 |
| Dicalcium phosphate dihydrate | 47.1 | 44.9 | 48.8 |
| Sodium monofluorophosphate | 0.753 | 0.720 | 0.77 |
| Sodium lauryl sulfate | 1.50 | 1.40 | 1.56 |
| Flavor | 1.0 | 0.95 | 1.03 |
| Anionic polyelectrolyte-Permasorb | 1.2$^a$ | 0.92$^b$ | 1.2$^b$ |
| Sodium saccharin | 0.19 | 0.18 | 0.20 |
| Glycerin | — | 5.15 | 5.36 |

-continued

|  | PARTS | | |
|---|---|---|---|
|  | A | B | C |
| pH | 6.5 | 6.5 | 6.5 |

<sup>a</sup>grade 10
<sup>b</sup>grade 30

The dentifrices are prepared by hydrating the anionic polyelectrolyte in the water/glycerine phase, followed by addition of ingredients other than sodium lauryl sulfate and flavor. The system is then mixed in a planetary mixer under vacuum and sodium lauryl sulfate and flavor are post-added.

| DENTIFRICE | VISCOSITY INITIAL VISCOSITY 10 RPM; #7 SPINDLE BROOKFIELD VISCOMETER MODEL RBF: 22° C. |
|---|---|
| A | 185,000 |
| B | 272,000 |
| C | 378,000 |

The viscosity levels were all of the high level which characterize a dentifrice of desirable creamy consistency.

The parts per million of total soluble fluoride retained by the dentifrices are as follows:

| DENT-FRICE | INITIAL | ROOM TEMPERATURE 49° C. | | ROOM TEMPERATURE 49° C. | |
|---|---|---|---|---|---|
|  |  | 3 WEEKS | 3 WEEKS | 6 WEEKS | 6 WEEKS |
| A | 990 | 890 | 660 | 910 | 540 |
| B | 1000 | 950 | 590 | 960 | 600 |
| C | 930 | 830 | 630 | 840 | 440 |

Desirable levels of total soluble fluoride are retained.

Highly desirable viscosity, excellent rheology and high total soluble fluoride retention are also obtained when Permasorb 10 (through 200 mesh) is employed.

In alternative embodiments the Permasorb material are replaced with other surface-treated polyelectrolytes as indicated above.

It is apparent that the above example illustrates the invention and various modifications may be made thereto.

I claim:

1. A dentifrice toothpaste or gel having a viscosity of about 50,000 to 420,000 cps (measured at 10 rpm with #7 spindle on Brookfield Viscometer Model RBF at 22° C.), said viscosity being sufficiently high so that said dentifrice is not liquid and runny and not so high that it is difficult to extrude from a dentifrice containing a normally water-insoluble dentally acceptable polishing agent, up to about 89.5% by weight of water and requiring added humectant and gelling agents, said dentifrice containing, as its sole essential humectant and gelling agent, a water-absorbent anionic polyelectrolyte polymer which provides and imparts both gelling and humectant characteristics to said dentifrice, said anionic polyelectrolyte polymer consisting essentially of a polyacrylic acid ionically complexed with a polyvalent metal cation selected from the group consisting of aluminum, zirconium, iron and zinc at a pH between 2.0 and 8.5 which pH is below the pH of reversibility of the ionic complex of said polyvalent cation and said water absorbent anionic polyelectrolyte, said ionically complexed polyelectrolyte polymer having a particle size such that at least about 90% of the particles are larger than 2 microns, each of said particles having a linkage density at the particle surface greater than the linkage density in the particle interior, the linkages at the particle surface comprising at least in part ionic complexing of said anionic polyelectrolyte polymer by said polyvalent metal cations, said anionic polyelectrolyte polymer being provided in said dentifrice in an amount of about 0.5–20% by weight, said dentifrice containing a humectant and gelling agent selected from the group consisting of: (a) said anionic polyelectrolyte polymer as the sole humectant and gelling agent; (b) said anionic polyelectrolyte polymer as the sole gelling agent and up to about 20% by weight of an additional humectant; (c) said anionic polyelectrolyte polymer as the sole humectant and up to about half the amount of said anionic polyelectrolyte polymer of an additional gelling agent; and (d) said anionic polyelectrolyte polymer with up to about 20% by weight of an additional humectant and up to about half the amount of said anionic polyelectrolyte polymer of an additional gelling agent; wherein said additional humectant and said additional gelling agent provide rheological modifications in the character of said dentifrice.

2. The dentifrice claimed in claim 1 wherein said polyvalent metal cation is selected from the group consisting of aluminum, zirconium and iron.

3. The dentifrice claimed in claim 1 wherein said anionic polyelectrolyte is present in amount of about 0.5–3% by weight.

4. The dentifrice claimed in claim 1 wherein said anionic polyelectrolyte is a polyacrylate and said polyvalent cation is aluminum.

5. The dentifrice claimed in claim 4 wherein said anionic polyelectrolyte has a particle size distribution such that about 0.0716% by weight of the particles are coarser than 149 microns; about 0.329% by weight are coarser than 74 microns; about 1.25% by weight are coarser than 44 microns and about 98.35% are finer than 44 microns and has a mean particle size of about 30 microns.

6. The dentifrice claimed in claim 4 and wherein additional humectant is present in addition to said anionic polyelectrolyte.

7. The dentifrice claimed in claim 6 wherein said humectant is glycerine.

8. The dentifrice claimed in claim 5 wherein said dentifrice includes a fluorine-containing compound in amount to provide about 0.01–1% by weight of fluorine to the dentifrice and said anionic polyelectrolyte is present in amount of about 0.5–2% by weight.

9. The dentifrice claimed in claim 8 wherein said fluorine-containing compound is sodium monofluorophosphate.

* * * * *